United States Patent
Hennig

[11] Patent Number: 5,919,228
[45] Date of Patent: *Jul. 6, 1999

[54] CORNEAL INSERT

[76] Inventor: Jürgen Hennig, Obere Hauptstrasse 3, 78532 Tuttlingen, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/672,149

[22] Filed: Jun. 27, 1996

[30] Foreign Application Priority Data

Jun. 27, 1995 [DE] Germany .......... 195 23 223
Aug. 18, 1995 [DE] Germany .......... 195 30 465

[51] Int. Cl.⁶ .......... A61F 2/14
[52] U.S. Cl. .......... 623/5; 606/107
[58] Field of Search .......... 623/4, 5; 606/107

[56] References Cited

U.S. PATENT DOCUMENTS 3,728,315  4/1973  Gustafson .
4,665,906  5/1987  Jervis .
5,466,260  11/1995  Silvestrini et al. .......... 623/5

FOREIGN PATENT DOCUMENTS 9406381  3/1994  WIPO .......... 623/5
9503755  2/1995  WIPO .......... 623/5

*Primary Examiner*—Randy C. Shay
*Attorney, Agent, or Firm*—Morrison & Foerster LLP

[57] ABSTRACT

A corneal ring for the correction of the refractive power of an eye consists or a part of metal or plastic which is formed into a split ring having at least one turn, or into a ring segment having a diameter of effective diameter matched to the periphery of the cornea of an eye. The ring or ring segment is inserted into a ring channel which is formed with a special instrument in the cornea of the eye and the radius or curvature of the ring or ring segment is subsequently adjusted by a laser beam, or by radiation, or electromagnetic induction, or magnetism to achieve a fine correction of the refractive power of the eye.

8 Claims, 10 Drawing Sheets

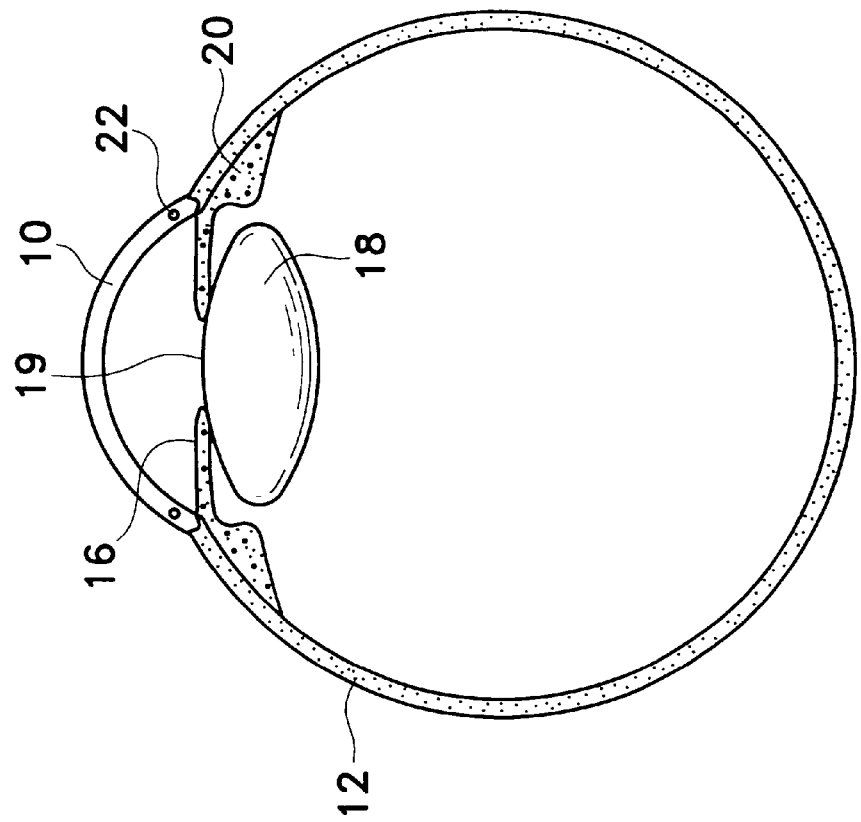
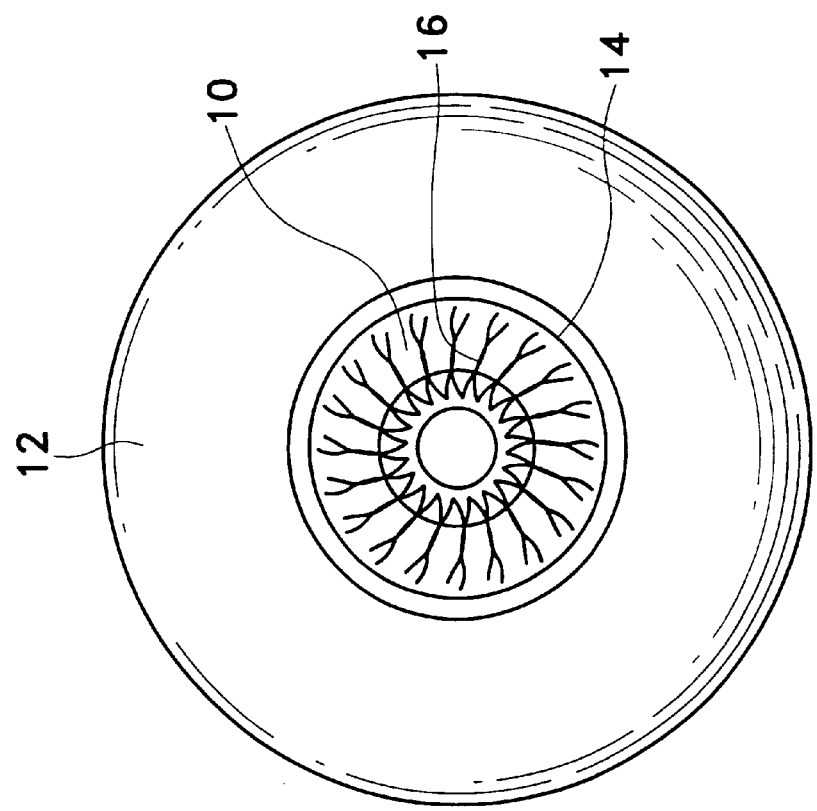

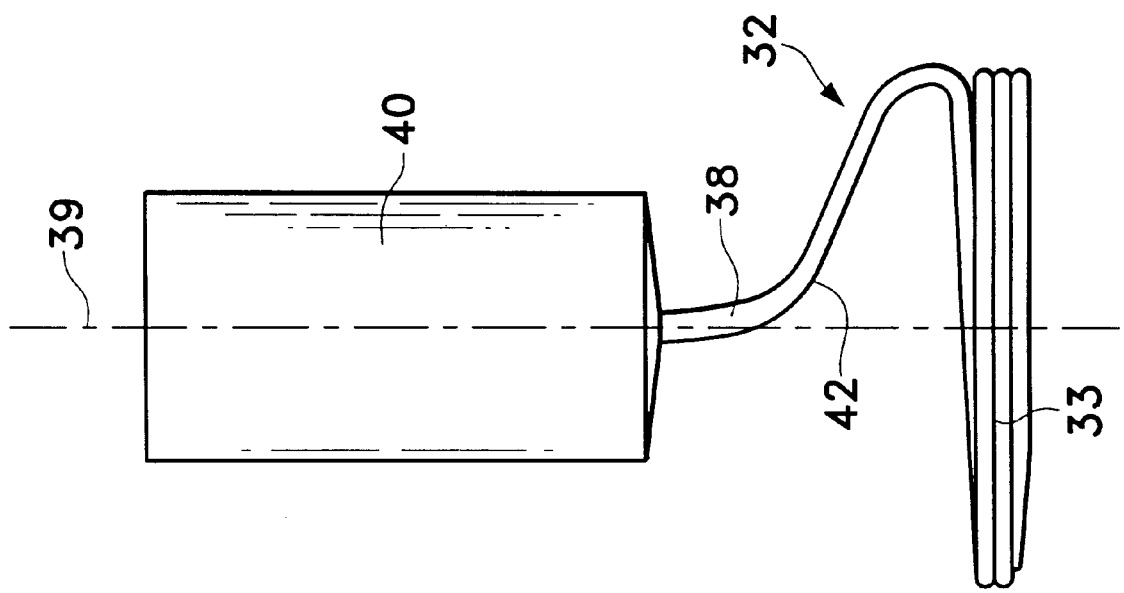

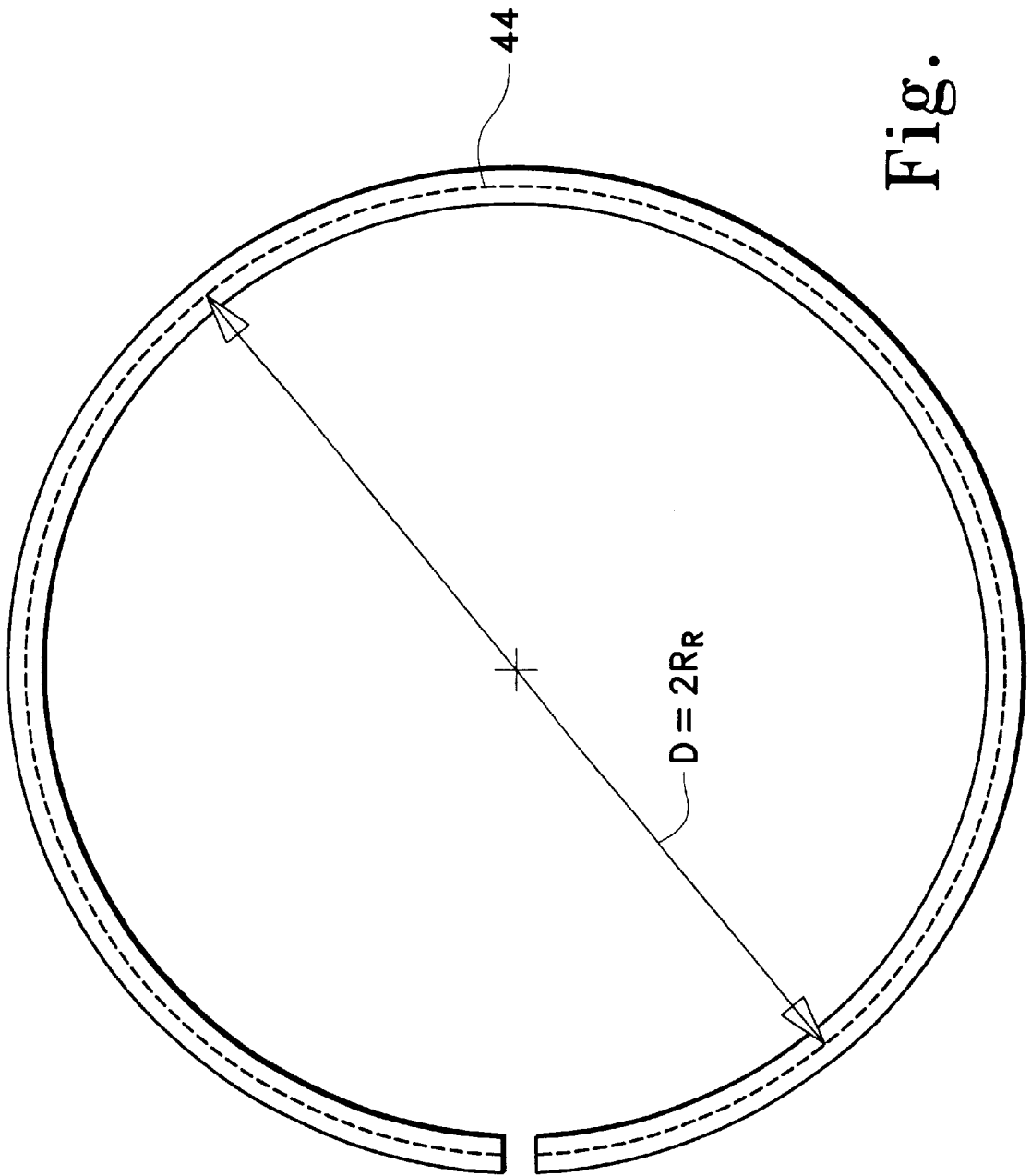

CORNEAL INSERT

FIELD OF THE INVENTION

The present invention relates to a corneal insert, to an instrument for cutting a ring-like channel, in particular within the periphery or the cornea or an eye, and a method for correcting the refractive power of the eye, or for compensating for refractive errors of an eye.

DESCRIPTION OF PRIOR ART

In the optical image-forming system of the eye, the cornea represents the part which is by far the most effective. The corneal surface forms the boundary surface between the air, with a low refractive index, and the corneal tissue with a high refractive index. Accordingly, even a small change of the radius of curvature of the cornea brings about a substantial change of the total refractive power of the eye.

This circumstance is the reason efforts have been made to heal defective vision, which hitherto made spectacles necessary, by surgical operations which are intended to change the curvature of the cornea. The previously used methods, such as radial keratotomy or photorefractive operations all have the decisive disadvantage that they produce irreversible changes at the eye and are in many cases, are not permanently successful. Another line of approach has been to change the curvature of the eye using so-called corneal rings, sometimes referred to as corneal ring inlays or inserts.

A summary of the prior art of keratorefractive surgical techniques and of corneal ring inlays is given in the introduction to the international application with the publication number WO 94/06504. Another summary is given in U.S. Pat. No. 5,391,201. U.S. Pat. No. 5,391,201 is more particularly concerned with a method of altering the curvature of the central optical region or the cornea or the eye or a patient comprising:

a) making a circular peripheral cut in the cornea, peripheral to the optical zone;
   b) undermining the stroma through Bowmann's membrane in a circular fashion;
   c) placing into the undermined portion of the stroma an inlay ring apparatus comprised of a bio-compatible, continuous ring of a material having a geometry effective for altering the curvature of a cornea;
   d) sealing the periphery of the tissue.

According to the disclosure of this U.S.-patent, the ring is inserted using the "tire-iron" approach which is understood to mean that the edge of the cornea is levered over the ring around the periphery of the ring.

Corneal rings themselves are described in a large number of patent applications. For example the international application published under the number WO94/03129 discloses a hybrid intrastromal corneal ring in the form of a split polymeric ring suitable for introduction into the stroma and comprising at least one outer layer of a low modulus, physiologically compatible polymer. Various techniques are disclosed for connecting the ends of the ring.

Furthermore, the international patent application with the publication no. WO94/06381 described a variety of different configurations of the end portions of split ring such that when allowed to come together the end portions intermesh and provide a ring with a smooth and continuous outer profile.

The further international patent application with the publication no. WO95/03755 relates to a segmented preformed intrastromal corneal insert In this case the insert, for which various examples are given, subtends only a portion of a ring or "arc" encircling the anterior cornea outside of the cornea's field of view. The application also describes a procedure for inserting the device into the cornea.

The international patent application with the publication number WO95/03747 is also concerned with an intrastromal corneal insert which comprises a pliable polymeric insert subtending less than 360° of the cornea's circumference. The application also describes a minimally invasive procedure for inserting one or more such inserts into the cornea. Another corneal ring is described in U.S. Pat. No. 5,323,788. This corneal ring has a flexible, preferably circular body, sized and configured such that it can be inserted into a human eye and comprised of a material which is compatible with human ocular tissue. The end portion of the circular body overlap each other and are formed in several different configurations or embodiments. The end portions are preferably configured such that when allowed to come together, they intermesh and provide a ring with a smooth and continuous outer profile.

U.S. Pat. No. 5,405,384 relates to an intrastromal corneal ring which is not uniform in dimension. It has, typically, two or more raised areas (or areas of additional bulk) spaced apart from each other on the ring. This ring design, when introduced into the stroma and properly adjusted there, permits at least partial correction or astigmatism in the eye. The adjustment referred to here relates to the adjustment of the ring in the direction or its circumference so that the astigmatism correcting portions of the ring are correctly positioned relative to the eye.

The international patent application with the publication no. WO88/10096 describes surgical apparatus for inserting a plastic split-end adjusting ring into the stroma of the cornea of the eye, wherein the adjusting ring includes, as a part thereof, a dissecting head 48 to part the stroma and provide a pathway for the adjusting ring as the ring is rotated. Here, the ends of the adjusting ring are moved to change the shape of the cornea to a desired shape in accordance with the desired visual correction after which the ends of the adjusting ring are fixably joined to maintain the desired shape.

Another technique for inserting a corneal ring is described in U.S. Pat. No. 4,671,276.

The system described there for adjusting the curvature of the cornea of the eye involves inserting a plastic split end adjusting ring into the stroma of the cornea above the corneal ring at about the eight millimeter chord, then inserting one end or a metal split end dissecting ring into the incision with the trailing end of the dissecting ring remaining outside the cornea. The one end or the dissecting ring has a transverse hole therein near its tip end. The dissecting ring is held by a magnetic holding and rotating device which has a concave end surface and a circular groove therein for receiving the metal dissecting ring and for holding it in a circular shape. As the holder is rotated the inserted end of the metal ring is magnetically forced to follow rotation of the holder. Thus the dissecting ring is inserted in a circular path within the stroma. A sled shaped end portion of the dissecting ring causes the moving inserted end of the dissecting ring to be biased upwardly toward the anterior of the stroma as the dissecting ring is rotatably inserted therein. When the inserted end of the dissecting ring reaches the first incision its rotation is stopped and a second incision is made over the transverse hole in the dissecting ring perpendicular to and intersecting one edge of the first incision. The plastic adjusting member also has a transverse hole near its one sled shaped end which is placed next to the first incision. A connecting link member is inserted through the holes in the ends of the respective dissecting and adjusting rings to releasably join the two rings, the rotational direction of the holding tool is then reversed which "backs out" the dissecting ring and at the same time pulls in behind it the plastic adjusting ring. When the now joined ends of the two rings are rotated back around to the insertion point, the now withdrawn dissecting ring is released from the adjusting ring. A corneascope type image of the corneal topography is displayed on a visual surface and compared to a desired target image. Adjustment is then made in the relative position of the ends of the adjusting ring to change the shape or the cornea to bring the image of the present shape into coincidence with the desired shape whereupon the two ends of the adjusting ring are fixedly joined to maintain the desired shape.

Another system of this kind is also described in U.S. Pat. No. 4,766,895.

The initially named international patent application with the publication No. WO94/06504 is also of particular interest since here corneal rings are inserted into the eye with the thickness of the ring being changed after its insertion into the eye in order to change the refractive power of the eye. Various examples for such corneal rings are given in this application. All involve mechanical adjustments of the ring, e.g. by making it in two concentric parts which are connected together by a thread.

The international patent application with the publication no. WO93/11724 describes the use of acoustic oscillations to enhance the cutting action of a surgical cutting tool. A surgical cutting instrument is described in U.S. Pat. No. 5,403,335.

OBJECT OF THE INVENTION

The object underlying the present invention is to provide a device and a method for correcting the refractive power or for compensating for refractive errors of an eye with the device being preferably removable and the method reversible and permitting fine and controllable corrections of the change of refractive power at any time with a small degree of effort and without the complications involved in the design of a mechanically adjustable ring of relatively small dimensions.

It is a further object of the present invention to provide an instrument which enables the insertion of the device, i.e. enables the method to be carried out.

BRIEF DESCRIPTION OF THE INVENTION

In order to satisfy this object there is provided a corneal insert in the form of a ring or ring segment for the correction of the refractive power of an eye consisting of at least one elongate part of metal or plastic which is formed into a ring with at least one turn, or into a ring segment, said ring or ring segment having a ring diameter which is matched to the diameter of the cornea and, for example, amounts to 6 to 12 millimeters, said ring or ring segment being made of a material such that the spring characteristics of the ring or segment in the sense of at least one of an expansion or contraction of said ring diameter are adjustable or finely adjustable after insertion by the action of radiation, in particular electromagnetic radiation such as laser light, or by a magnetic treatment, or by an inductive treatment.

The method of the invention for correcting the refractive power of an eye or for compensating for refraction errors comprises the steps of cutting a ring-like channel into the periphery of the cornea, of introducing an elongate member of metal or plastic which can be formed into a segment or a ring having at least one turn with a diameter matched to that of the periphery of the cornea into the channel, and or effecting at least the fine correction of refractive errors after the insertion of the segment or ring is effected, is characterised in that the ring is comprised of a material which can be expanded and/or contracted after insertion by the action of radiation, in particular electromagnetic radiation such as laser light, thermal radiation, electromagnetic induction or magnetism, and in that the said fine correction is effected in situ in the eye by the use of such radiation in particular electromagnetic radiation such as laser light, thermal radiation, electromagnetic induction or magnetism.

In other words, a ring-like channel is first provided in the periphery of the cornea. This channel should be precisely centred and lie at approximately half the depth of the cornea, in the stroma.

Prior to withdrawing the instrument a thin ring with approximately the same diameter as the channel which has been provided is secured to the tip of the instrument and is drawn into the channel by the instrument on retracting the same.

Should it become desirable at some time to restore the original state then it is sufficient to simply remove the ring.

Generally speaking, the characteristics or the ring, in particular its spring tension in the installed state, will have been selected to effect a coarse change of the refractive power of the eye. For example, an increase of the spring tension will increase the flattening of the cornea and vise versa. According to the present invention the fine adjustment then takes place through the intentional and precisely metered application of, for example, laser energy to the ring which make it possible to change both its volume and also its length and tension within certain limits. That is to say, a correction of the faulty vision through changing the curvature of the cornea expediently takes place in two steps:

1. Coarse correction by the insertion of a corneal ring having a previously calculated diameter or spring tension.
2. Fine correction after healing of the surgical wound with the ring in place in the eye and the disappearance of any initially existing tissue strains. This fine correction can, for example, take place by the use of a laser while checking the optical parameters of the total eye with the aid of a suitable refractometer. The use of a data processing plant or a computer to coordinate and steer the laser is advantageous.

However, initial experiments with the corneal insert of the invention have shown that the range of adjustment which can be achieved is substantial so that the insert may be first inserted, with both the coarse and fine adjustments then being made within the eye, i.e. separate coarse adjustments prior to insertion of the ring may not be necessary, which has the advantage that the ring can be made with the same diameter at the ring channel which facilitates the insertion or the insert.

BRIEF LISTING OF THE FIGURES

The invention will subsequently be explained in more detail with reference to embodiments and to the drawings in which are shown.

FIG. 1 a schematic illustration of the human eye in the form of a front view,

FIG. 2 a schematic illustration of the human eye in the form of a median section, FIG. 3 a side view of an instrument for forming a ring channel within the periphery of the cornea, FIG. 3A is a side view of an instrument for forming a ring channel wherein the instrument has a plurality of turns, FIG. 4 the instrument of FIG. 3 seen from above, FIG. 5 the instrument of FIG. 3 seen from below, FIG. 6 an enlarged illustration of the parting and cutting tip of the instrument of FIGS. 3 to 5, with the tip being shown enlarged in the ratio 1:3 with respect to the size in FIG. 5, FIG. 7 a plan view of a simple non-closed split ring, FIGS. 8 and 9 two drawings to explain the correction of myopia using the ring of the invention, FIGS. 10 and 11 two drawings to show the correction of hyperopia using the ring of the invention, FIG. 12 a view similar to that of FIG. 7 to explain the detailed construction of one possible embodiment of the invention, with FIGS. 12a, 12b and 12c showing alternative cross-sections for the ring of FIG. 12, FIG. 13 a figure similar to FIG. 12 showing a similar ring in accordance with the invention, with cross-section of this further ring being shown in FIGS. 13a, 13b and 13c, and FIG. 14 a ring segment in accordance with the present invention.

FIG. 15 is a plan view of a ring having a plurality of turns.

DESCRIPTION OF PREFERRED EMBODIMENTS

Figure 4:
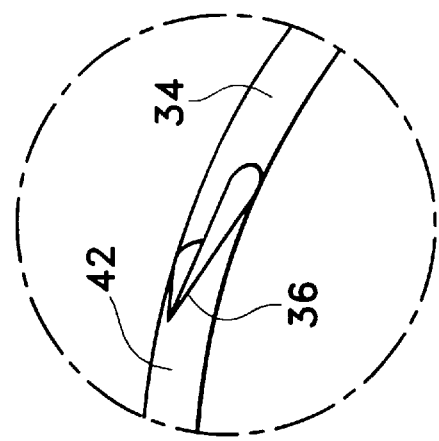
Figure 6:
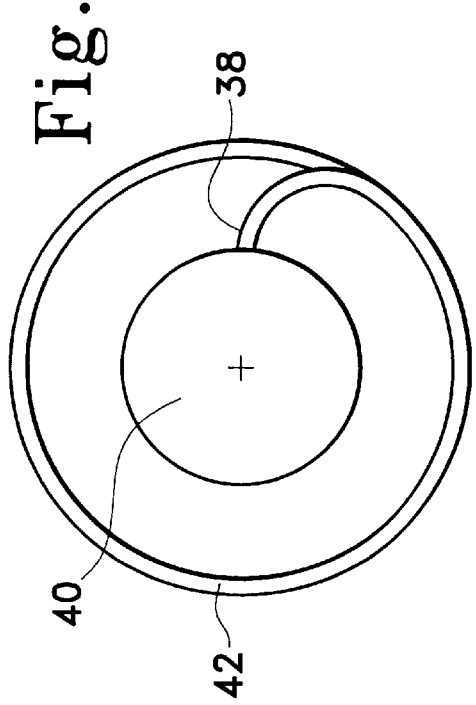
Figure 5:
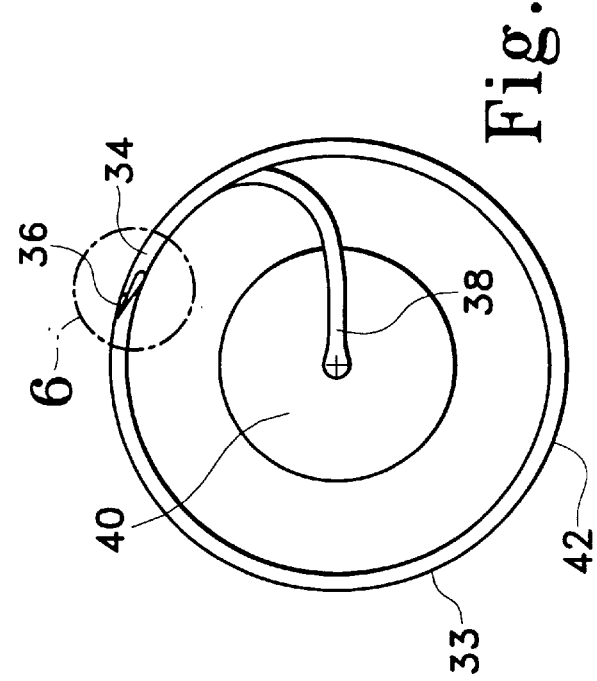

FIGS. 1 and 2 serve to explain generally the layout of the human eye, at least in the region of the cornea which is particularly important for the present invention. In this representation the cornea is characterised by the reference numeral 10 and forms the boundary surface with the air in the area of the pupil. The cornea has a pronounced effect on the total refractive power of the eye. The cornea merges into the so-called sclera 12 or the eye and the peripheral region of the cornea 14 is located directly in front of this transition. The periphery of the cornea lies approximately coaxial to the lens 18 and to the pupil 19. Within the peripheral region of the cornea there is located the iris 16 and beneath it the lens 18 with the ciliary body 20 to the left and right of it in FIG. 2.

In FIG. 2 there is shown the ring-like channel 22 into which a corneal ring has to be inserted in accordance with the present invention.

Figure 3:
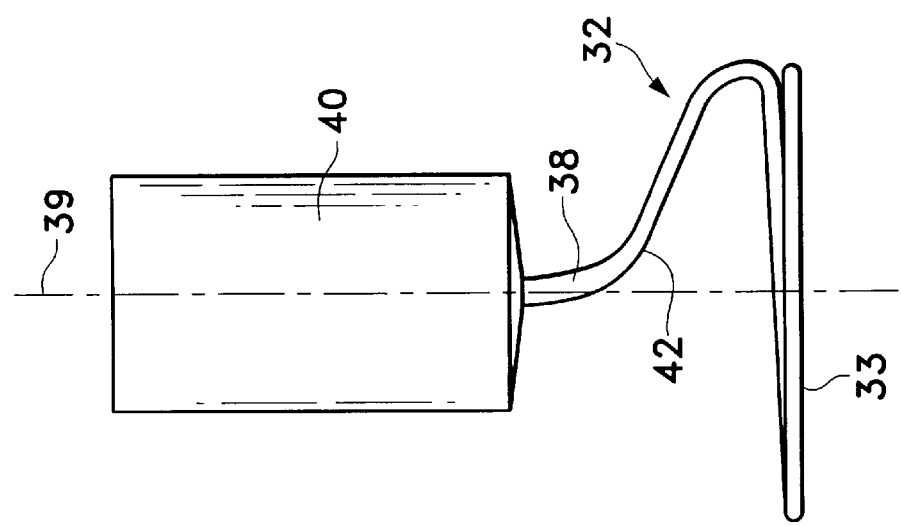

This channel must first be cut prior to insertion of the ring. This takes place in accordance with the invention with the tool of FIGS. 3 to 6. As can be seen from these Figures, the instrument has a working and 32 which consists of at least one turn 33 (FIG. 3 showing one turn and FIG. 3 showing more than one turn) of an at least substantially helical wire resembling one turn of a thread and having at its one end 34 a cutting tip 36 and merging at its other end into an actuating part in the form of a handle 40. The wire section 38 leading to the actuating part or handle extends substantially coaxial to the helical turn.

This special form of the working end is necessary in order to insert the tip into the cornea at a position around the pupil and thereafter to move it in a circular track within the cornea, which is necessary for the formation of the channel without cutting through the cornea at the surface or the eye all around the pupil.

The handle 40 is formed as a vibratory generator and causes an oscillation around the central longitudinal axis 39 of the instrument or of the handle in such a way that the cutting tip swings to and fro in the direction of the ring-shaped channel, i.e. the oscillations are angular oscillations around the longitudinal axis 39. Here, the oscillation should have a substantially higher frequency than the natural frequency of the handle or of the eye, and indeed a frequency which is preferably substantially the same as the natural frequency of the cutting tool. The sense of this very important embodiment is to reduce the cutting resistance and thereby to facilitate the guidance of the instrument and the execution of the surgical work by the surgeon.

Although it is preferred to guide the instrument by hand, possibly using an optical enlargement or imaging system, it would, however, also be conceivable to mechanically move the actuating part, for example by a correspondingly programmed robot hand, optionally under control by a computer or by a surgeon.

The cutting tip of the instrument cuts the ring channel at the half depth of the cornea and displaces the cornea to all sides of the cutting wire. However, no material is preferably cut out, i.e. the working tip has a pure parting function.

After the cutting of the ring channel, the cutting tip returns again to the position of insertion and can there be connected to one end of an elongate part which forms the corneal ring (for example the corneal ring 44 of FIG. 7). The nature of this connection is not shown here. The attachment could take place in various ways. It could e.g. by brought about in such a way that the working tip is connected via a sleeve-like mount to one end of the elongate part forming the ring.

It would also be conceivable to provide a transverse bore (not shown) in the cutting tip and to push a fine pin through this transverse bore and through the one end of the (split) ring. A spring ring could also be used in order to clamp the one end or the split ring to the cutting tip and the cutting tip could have an abutment or ring shoulder behind the cutting tip to enable the reliable attachment to it of the corneal ring. Alternatively, the actual cutting tip could be removable leaving behind it a socket into which the one end of the split corneal ring is inserted and then secured in same way, for example by a small transverse pin.

On turning back the instrument, the elongate part which has preferably previously been formed into an open ring 44 can be drawn into the ring channel 22.

The corneal ring 44 is so formed that it can be subjected to at least a fine adjustment after insertion into the eye in order to set the precise curvature of the cornea and thus the refractive power of the eye. Many conceivable possibilities exist for the realization of ouch a fine adjustment.

One particularly interesting possibility lies in using a plastic for the ring in which small bubbles can be generated on laser irradiation in order to hereby achieve a controllable change of the characteristics of the ring.

This possibility will now be explained in more detail with reference to the FIGS. 8, 9, 10 and 11.

Figure 8:
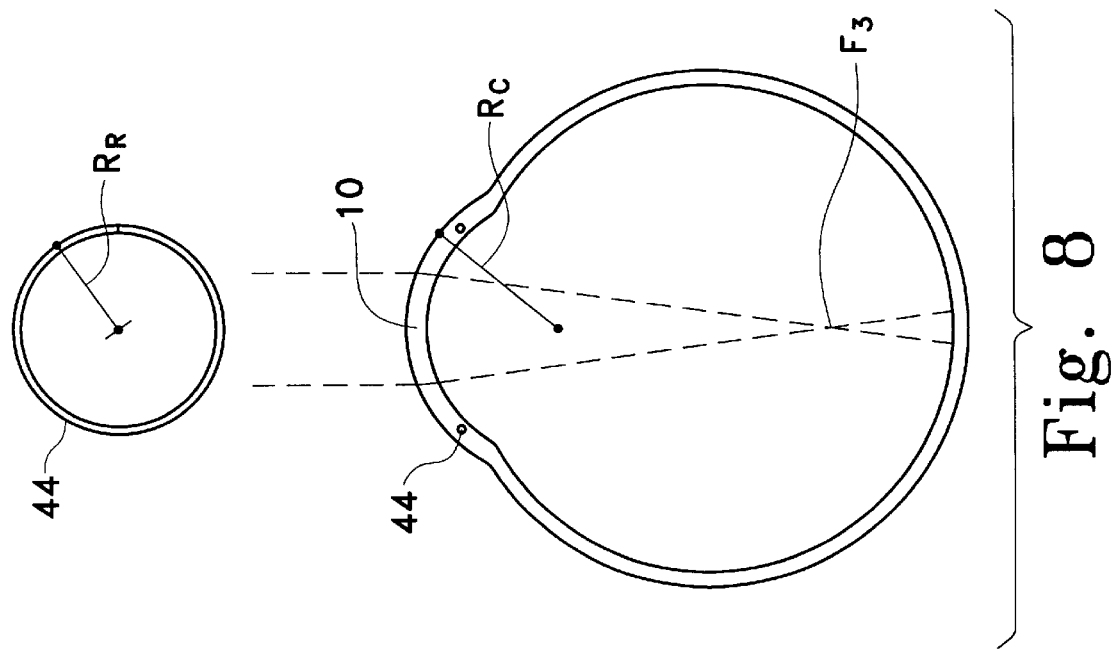

Turning first to FIG. 8 this drawing shows a schematic median section through the eye similar to FIG. 2, with a corneal ring 44 having been inserted into the stroma in the peripheral region of the cornea 10. This ring was initially dimensioned to be a closed ring and was chosen to partially, but not fully correct the myopia from which the patient is suffering. The corrected vision using the ring results in the eye focusing incoming light at the point F3 in front or the retina.

it will be noted that the cornea has an effective radius Rc. the corneal ring 44 has a radius of Rr.

Figure 9:
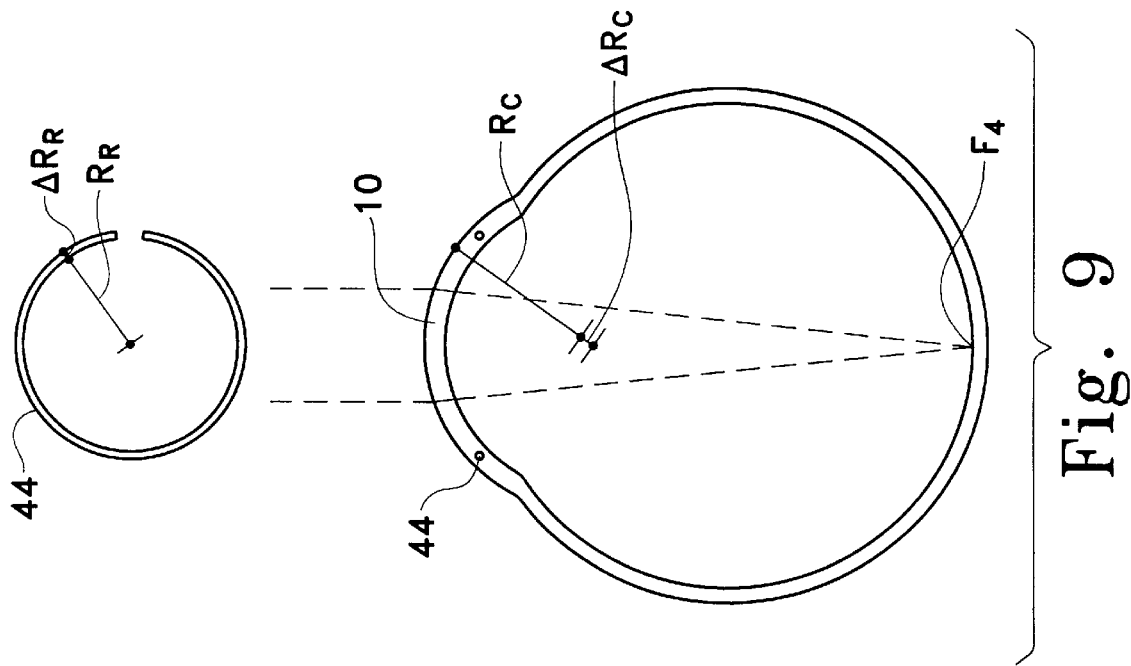

In order to correct the residual myopia, it is necessary to flatten the cornea somewhat so that Rc changes to Rc+Δ Rc as shown in FIG. 9 which results in the incoming light being focused at F4 on the retina.

To achieve this flattening of the cornea, it is necessary to cause the ring 44 to expand somewhat as shown to the left in FIG. 9. That is to say, the ring has to be acted on in some way to change its radius from Rr to Rr+Δ Rr, which necessarily also results in the distance between the two ends of the split ring increasing, which can again be seen in FIG. 9. It will be noted from FIG. 9 that with the change in the radius of the ring and the associated partial flattening of the cornea, the myopia has now been fully corrected and the incoming light is accurately focused on the retina of the eye.

Figure 11:
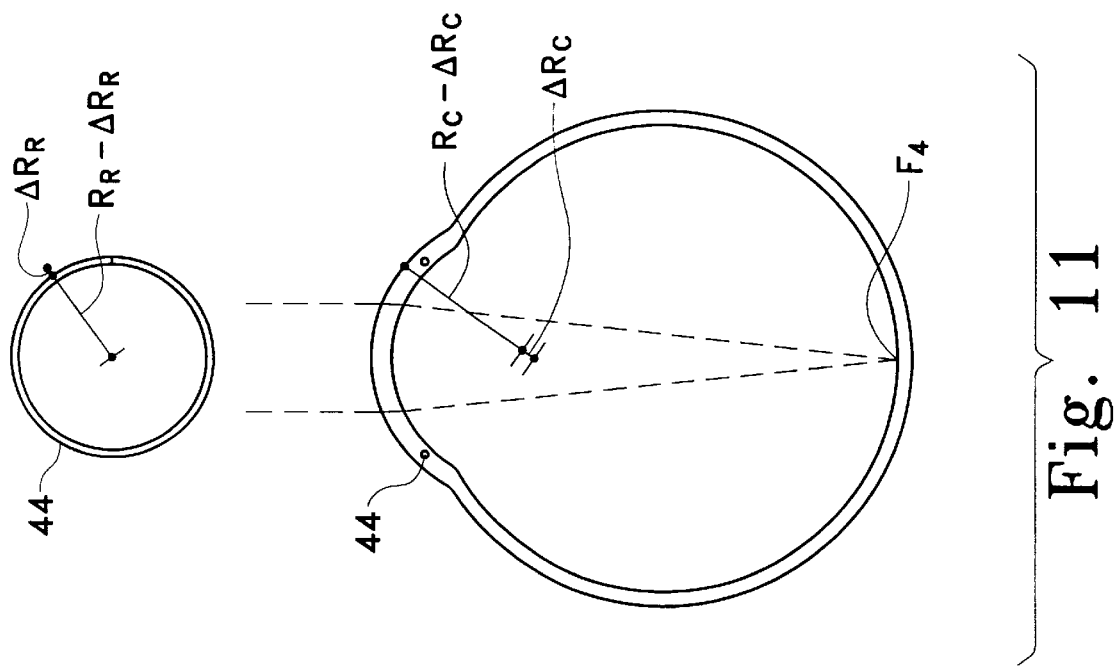
Figure 10:
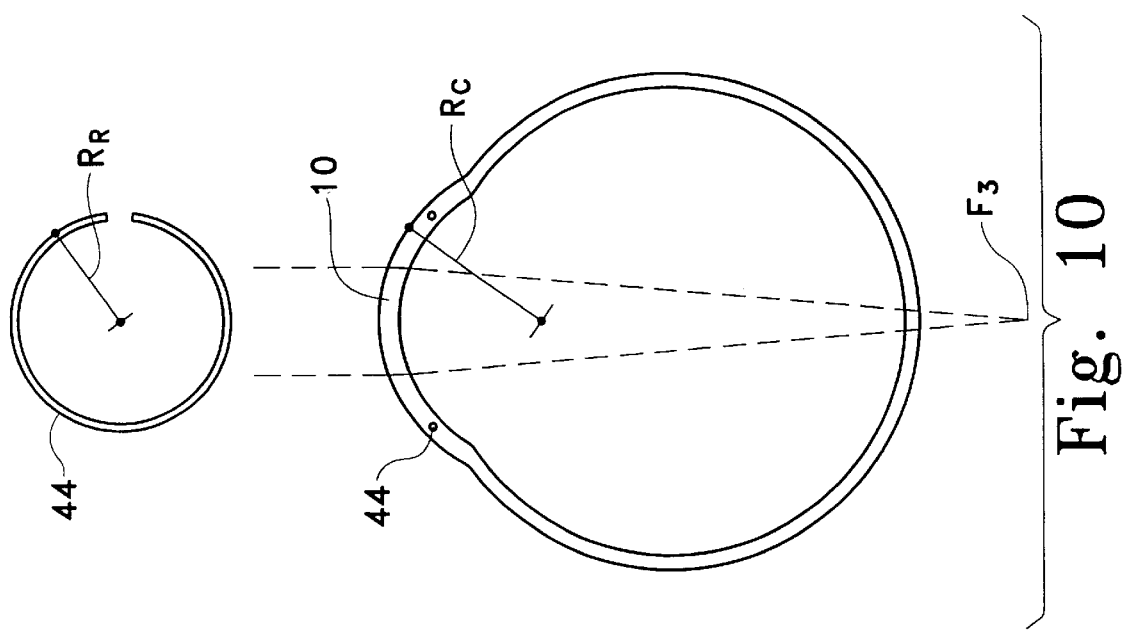

FIGS. 10 and 11 show the similar situation when treating a patient suffering from hyperopia. In this case, as seen in FIG. 10, an initial correction has been made by selecting a corneal ring 44 which has reduced the degree of hyperopia so that light entering the eye is focused at a notional point F3 behind the retina. The patient is thus still suffering from hyperopia, but to a lesser degree. In this case the radius of the cornea is also designated by Rc and it will be noted that the radius of the ring is again Rr but in this case the ring has a certain spacing between its two ends.

The ring is now treated, for example in a manner which will be later described, to reduce its radius to Rr−ΔR which results in partial or complete closing of the spacing between the two ends of the ring 44 (as shown in FIG. 11) and reduces the radius of the cornea from the previous value Rc to Rc−ΔRc. This changes the focus of the incoming light to F4, which is again on the retina of the eye, so that the patient once again has correct vision.

Various specific possibilities for changing the radius Rr of the corneal ring 44 will now be described with reference to FIGS. 12 and 13. These figures show the nominal diameter D of the corneal ring equal to 2Rr.

Figure 12A:
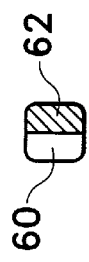
Figure 12B:
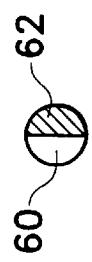
Figure 12C:
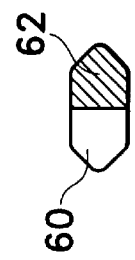
Figure 12:
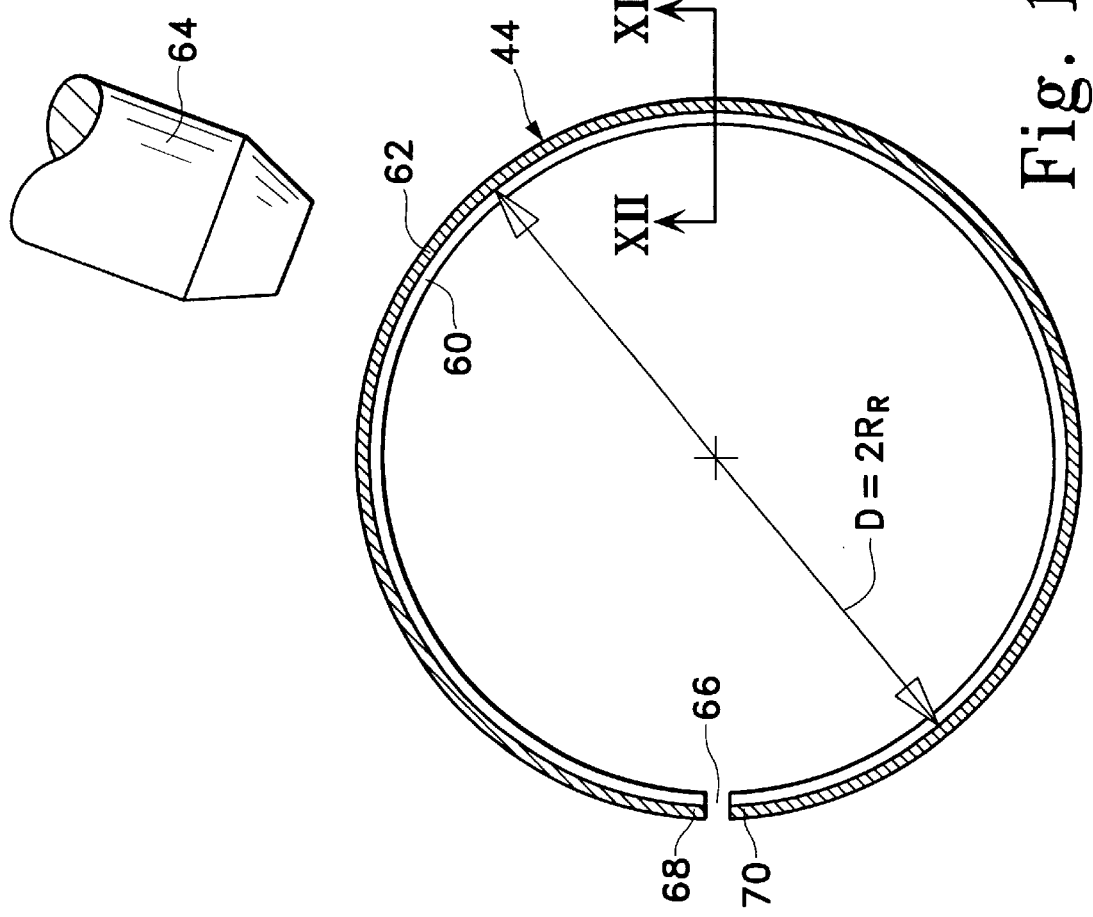

FIG. 12 shows a corneal ring 44 in the form of a split ring which, in thin case, should be thought of as a radially inner portion 60 and a radially outer portion 62. In a first variant the unitary material ring consists of one material, for example PMMA (polymethylmethacrylate) and it can for example have a square cross-section as shown in FIG. 12a (with rounded corners) or a round cross-section as shown in FIG. 12b. It can also have any other desired cross-section, for example a cross-section comprising an elongated diamond as shown in FIG. 12c, with the ring then having a shape resembling that of a shallow cone section which is indicated in FIG. C by the inclined position of the cross-section.

The reference numeral 64 designates the optical system of a laser which can be used to heat the material of the ring 44. The laser can for example be a Neodyn YAG laser. If the PMMA material is treated with a focused laser beam, then tiny bubbles are generated in it at the focus of the laser beam, which are thought to be due to local internal melting of the material, and these bubbles remain permanently in the material and lead to an expansion of the material.

If the laser beam is directed onto the radially inner portion 60 of the corneal ring 44, then the bubbles formed therein will cause this inner layer to expand relative to the outer layer which will cause the ring as a whole to expand, thus increasing the diameter or the ring and achieving a way of correcting myopia as shown in FIGS. 8 and 9.

Alternatively, if the treatment is restricted to the outer ring portion 62 then the expansion of this outer ring relative to the inner ring will cause the radius of the ring 44 to reduce in size, or to attempt to reduce in size, thus providing a way of correcting for hyperopia in accordance with FIGS. 10 and 11. Clearly, ir the ring is to contract, then a larger gap 66 has to be provided initially between the two ends 68 and 70 of the ring than is shown in FIG. 12.

It is not necessary for the laser beam to heat either the inner or outer ring portions 60, 62 over their entire length. On the contrary, discrete regions of the inner or outer portions of the ring will typically be treated with the laser beam causing just these regions to expand. As noted above, expansion only at the inner side leads to opening of the ring, that is to say the stress in the ring increases in the endeavour to open the ring. The radius of the ring increases and the curvature of the cornea is flattened. The degree of expansion of the ring depends on the intensity of treatment of the inner ring portion, i.e. on the number of bubbles produced. This can be very gradually controlled, preferably achieving a uniform distribution of the bubbles around the entire inner periphery of the ring, so that fine control of the adjustment is possible.

Clearly this is equally possible when reducing the radius of the ring by treatment of the outer ring.

Figure 13A:
Figure 13B:
Figure 13C:
Figure 13:
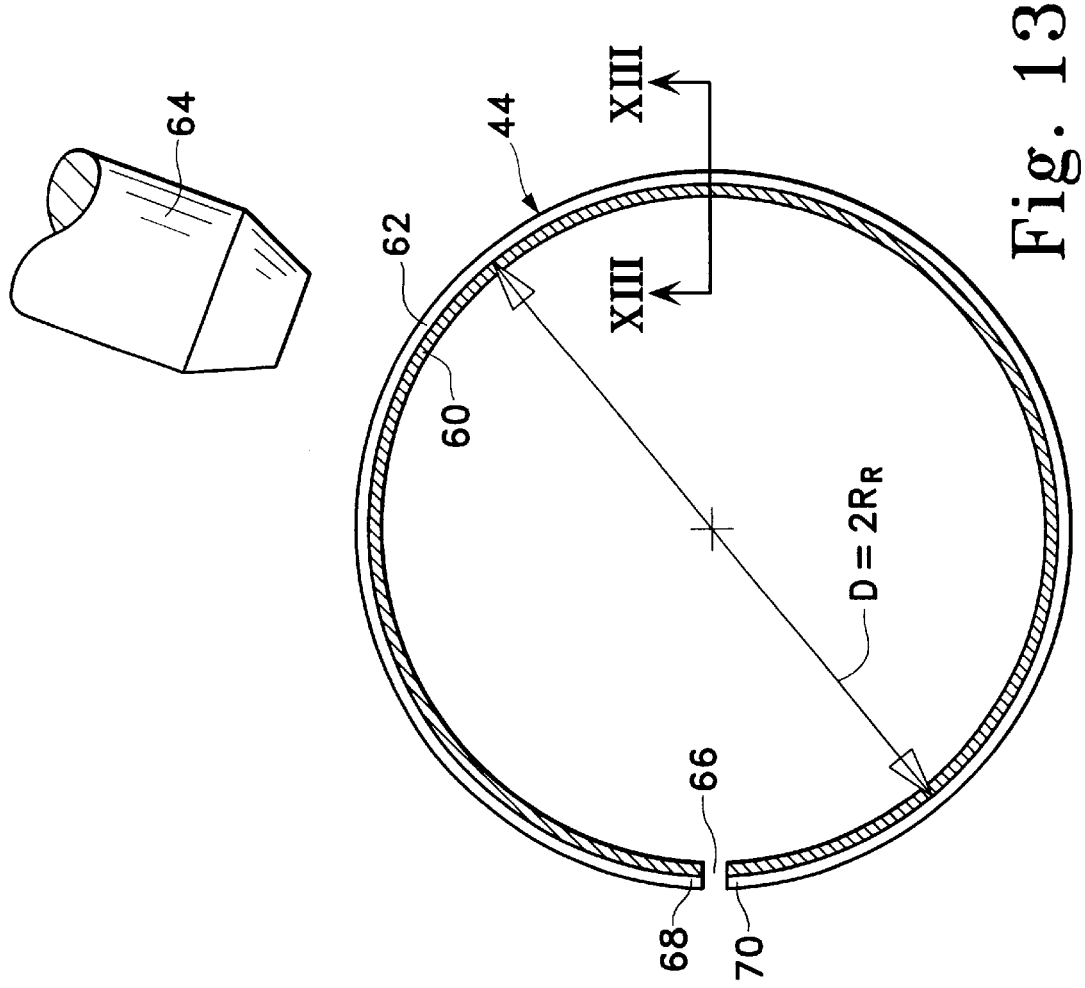

FIG. 13 shows essentially the same ring as in FIG. 12 with respect to the plan view of the ring and the possible cross-sectional shapes. This is again a unitary ring, however, it is a composite ring which now consists of two different materials. More specifically, the inner ring portion 60 consists of PMMA as before and the outer ring portion 62 consists of PVC with amorphous or crystalline components.

PVC is a material which shrinks when heated. Thus, in the present case, heating of the outer ring portion 60 of PVC causes shrinkage of the PVC and thus changes the stress in the ring in the sense of opening of the ring and increasing the radius of the ring. This ring is thus suitable for the correction of myopia in accordance with FIGS. 8 and 9.

The heating of the PVC can again be effected with a focused laser beam.

Since the inner ring portion 60 consists of PMMA, it is also possible to simultaneously heat-treat this material to generate bubbles therein which leads to expansion of the inner ring portion, thus enhancing the effect of contraction of the outer ring portion and substantially increasing the range of expansion that is possible for the ring as a whole.

In an alternative embodiment, the inner ring portion 62 could be formed of PVC and the outer ring portion bonded to it of PMMA. In this case, heating of the inner PVC ring will cause it to shrink and thus change the stress in the ring in the sense of contraction of the ring and reduction in the size of the radius. A ring of this kind would, for example, be useful for correcting hyperopia in accordance with FIGS. 10 and 11. If the ring is to contract, the gap 66 between the two ends 68 and 70 of the ring must naturally be wider than is shown in FIG. 13.

Again, an enhanced range of contraction can be obtained by using the laser to also generate bubbles in discrete regions of the outer ring portion 62.

It would also be possible to make the unitary ring of FIG. 12 of PVC only and to effect expansion or contraction of the ring by shrinkage of the inner and outer portions respectively.

The invention is not restricted to the use of PVC as the material which shrinks. Other plastics are believed to exist which, in similar fashion to PVC, have amorphous components and regularly arranged (crystal) components. On being heated, the amorphous components of the plastic change into more regular structures and these have a smaller volume than the amorphous structures which is the reason the material shrinks.

Equally, it is believed that PMMA is not the only material in which bubbles can be formed by focusing laser light onto regions within the material. Any other plastic material in which bubbles form when heated under laser light can also be used, providing it in compatible with the tissue of the cornea.

Materials are also known whose state of strain changes in step-like manner on being heated. These are the so-called "memory metals", such as for example nitinol.

Such materials can also be used to form corneal rings or corneal segments. Thus, a wire of nitinol can be formed into an open ring having a specific radius. If the temperature of the material is raised to above a critical temperature, the step temperature, then the shape, i.e. the size of this open ring, is impressed on the material, i.e. is so to say stored by the material. If the material is now cooled down to below the step temperature and bent into a ring with a smaller radius, it will retain this radius until heated above the step temperature, when it recalls the form impressed on it with the larger radius and expands again to this radius.

With a ring structure it is possible to vary the degree of expansion by heating only small areas of the ring locally to a higher temperature. Only these regions then expand and depending on the extent of the total number of small regions heated it is possible to control the precise size to which the ring expands.

The precise composition of the titanium nickel alloy selected should be chosen so that the step temperature lies slightly above normal body temperature. This will ensure that the ring does not expand to its full size simply by the normal temperature of the body, but only when regions of the ring are heated by incident radiation, for example laser light, to a temperature above the step temperature. By keeping the step temperature only slightly above body temperature, it is also possible to ensure that the eye is not damaged by the heat required to locally warm the ring.

The ring can have a shape as shown in any of the FIGS. 12, 12a, 12b, 12c.

The heating can also be effected by means other than laser light. For example, the heating could be effected inductively.

Figure 14:
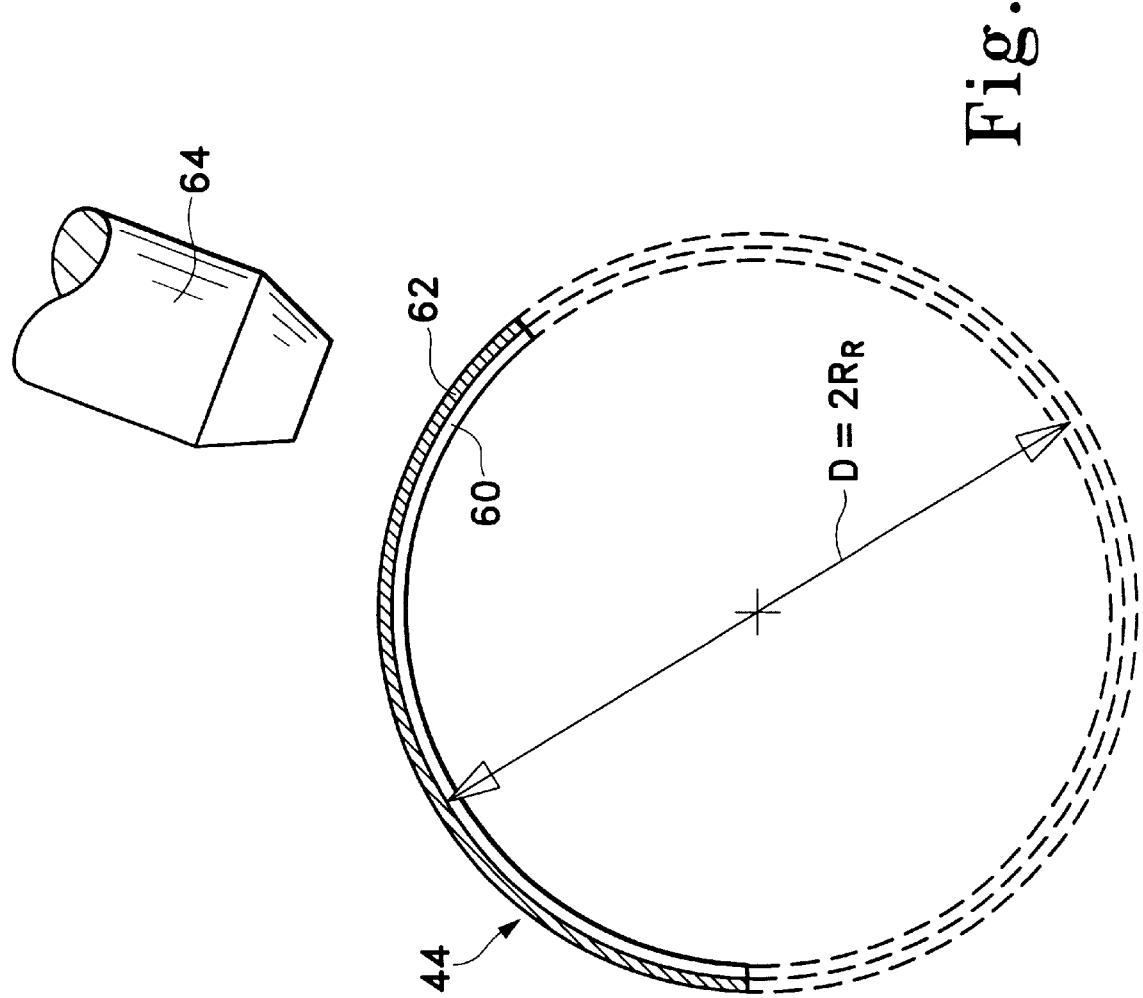

The corneal rings 44 described here hitherto have only one turn. It is, however, also conceivable to use ring segments to effect a local change in the curvature of the cornea, for example for the correction of astigmatism. Such a corneal ring segment is shown in FIG. 14. The use of such corneal segments is also described in the international patent application with the publication no. WO95/03755.

Figure 15:
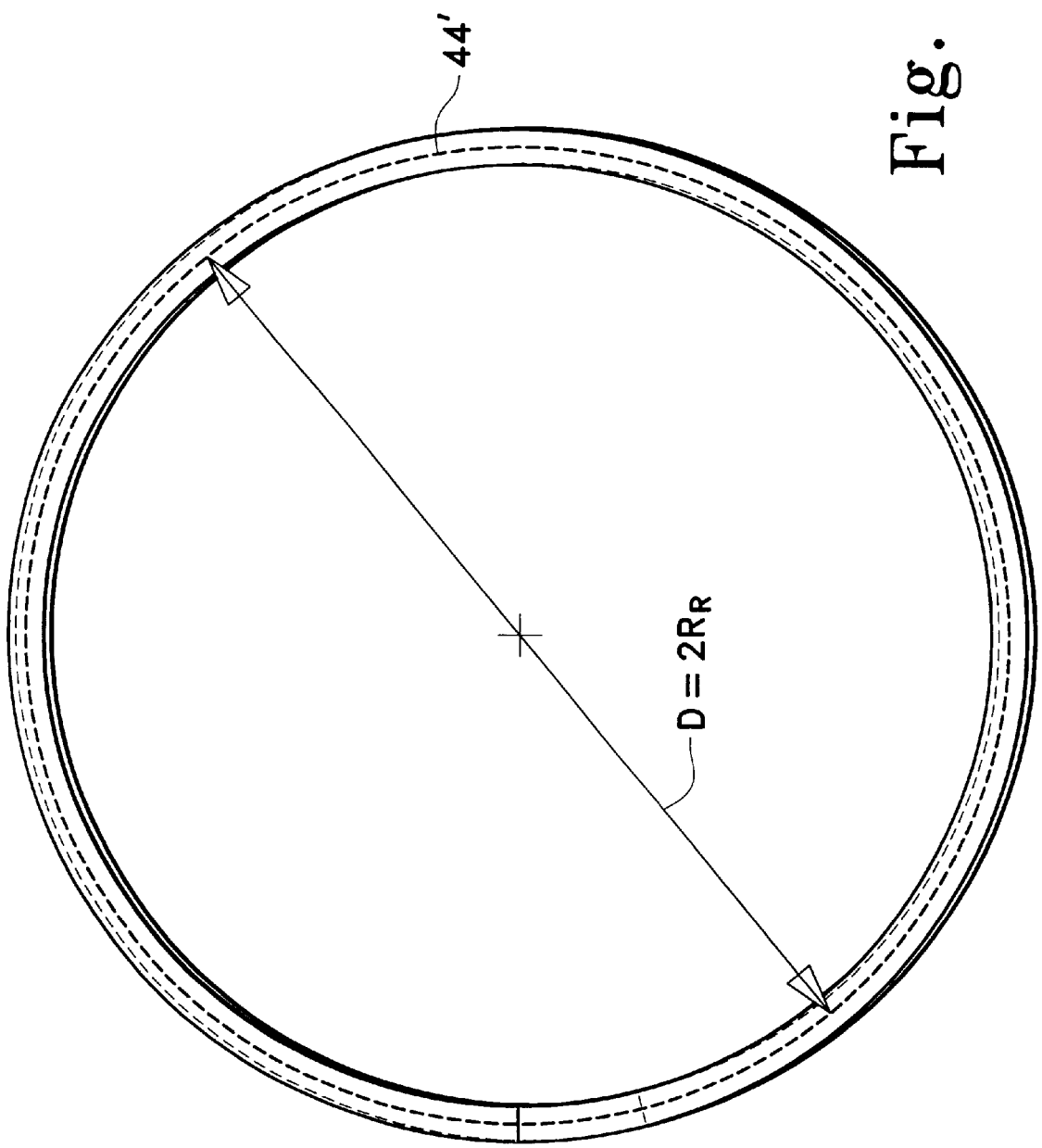

The corneal ring 44 described previously has only one turn. The ring can, however, also be provided with a plurality of turns if required, as shown in FIG. 15, for example, although this is not considered necessary.

Other possibilities also exist for providing a corneal ring or ring segment which could be used for the present invention. For example, another possibility lies in forming the corneal ring in a polymerisable plastic and setting the degree of the polymerization through a laser treatment, it being known that the spring and strength characteristics of a polymerisable plastic depend on the degree of polymerization.

Alternatively, the ring could consist of plastic which includes small bubbles which can be set under pressure on being heated up by means of a laser in order to bring about a permanent stretching of the ring in the sense of an enlargement of its diameter. When this variant is selected then the ring should first be made somewhat too small in order to be able to make use of the possibility of adjustment.

It would also be conceivable to set the spring constant of a ring consisting of metal by intentional thermal treatment by means of a laser, with the metal then best being arranged within a plastic coating which protects the eye from the heat during the thermal treatment. Such a plastic coating would also prevent direct contact between the metal and the tissue of the eye, thus preventing any possibility of the metal irritating the tissue.

It is also conceivable to form the ring from a bi-metallic strip which responds sensitively and permanently to introduced heat.

Designs are also possible in which different magnetic domains are retrospectively formed or changed in order, in this manner, to adjust the spring characteristics of the ring and thus to bring about a fine adjustment.

Although the invention is initially seen as a way providing a fine correction of the refractive power of an eye, initial experiments have shown that the degree of expansion or contraction which can be achieved are sufficiently great that in many cases the ring used for both coarse and fine correction, i.e. a separate coarse correction would not be necessary.

I claim:

1. A corneal insert for the correction of the refractive power of an eye, the insert comprising at least a segment of a ring, wherein at least a portion of the at least a segment of a ring comprises a memory metal.

2. A corneal insert in accordance with claim 1, wherein the memory metal comprises a first shape impressed therein at a temperature above a step temperature, the at least a segment of a ring having a first radius of curvature below the step temperature, and at least a select area of the memory metal attempts to adopt the impressed first shape when the at least a select area is caused to reach a temperature above the step temperature, thereby causing the at least a segment of a ring to have a second radius of curvature, the second radius of curvature being unequal to the first radius of curvature.

3. A corneal insert in accordance with claim 1, wherein the memory metal comprises nitinol.

4. A corneal insert for the correction of the refractive power of an eye, the insert comprising:
   at least one portion in the form of at least a segment of a ring, a radius of curvature of the at least a segment of a ring being in the range of about 6 to 12 millimeters;
   wherein the at least one portion comprises at least a segment of memory metal.

5. A corneal insert in accordance with claim 4 wherein the at least one elongate portion is a split ring comprising only one turn, and wherein ends of the elongate portion are not fastened to one another.

6. A corneal insert in accordance with claim 4 wherein the at least a segment of a ring comprises a first shape impressed therein at a temperature above a step temperature, the at least a segment of a ring subsequently comprises a smaller radius below the step temperature, and at least a select area of the at least a segment of a ring attempts to adopt the impressed first shape when the at least a select area is caused to reach a temperature above the step temperature.

7. A corneal insert in accordance with claim 4 wherein the at least one portion comprises a ring including a plurality of turns.

8. A corneal insert in accordance with claim 4, wherein the memory metal comprises nitinol.

* * * * *

UNITED STATES PATENT AND TRADEMARK OFFICE

CERTIFICATE OF CORRECTION

PATENT NO. : 5,919,228

DATED : July 6, 1999

INVENTOR(S) : Jürgen Hennig

It is certified that error appears in the above-identified patent and that said Letters Patent is hereby corrected as shown below:

Column 10, line 46, delete [6 to 12] and insert --3 to 6--

Signed and Sealed this

Twentieth Day of June, 2000

Attest:

Q. TODD DICKINSON

Attesting Officer

Director of Patents and Trademarks